United States Patent
Venneti et al.

(10) Patent No.: US 11,937,911 B2
(45) Date of Patent: Mar. 26, 2024

(54) SYSTEMS AND METHODS FOR ANALYZING AND MONITORING LUNG FUNCTION USING VOICE AND BREATH SOUND SAMPLES FOR RESPIRATORY CARE

(71) Applicant: DeepConvo Inc., Pittsburgh, PA (US)

(72) Inventors: Satya Venneti, Pittsburgh, PA (US); Mir Mohammed Daanish Ali Khan, Pittsburgh, PA (US); Rajat Kulshreshtha, Pittsburgh, PA (US); Prakhar Pradeep Naval, Pittsburgh, PA (US)

(73) Assignee: DeepConvo Inc., Pittsburgh, PA (US)

( * ) Notice: Subject to any disclaimer, the term of this patent is extended or adjusted under 35 U.S.C. 154(b) by 142 days.

(21) Appl. No.: 17/105,332

(22) Filed: Nov. 25, 2020

(65) Prior Publication Data
US 2021/0153772 A1 May 27, 2021

Related U.S. Application Data

(63) Continuation-in-part of application No. 16/931,429, filed on Jul. 16, 2020.

(60) Provisional application No. 62/941,477, filed on Nov. 27, 2019.

(51) Int. Cl.
*A61B 5/08* (2006.01)
*A61B 5/00* (2006.01)
*G06N 20/00* (2019.01)

(52) U.S. Cl.
CPC .......... *A61B 5/0816* (2013.01); *A61B 5/7203* (2013.01); *A61B 5/7275* (2013.01); *A61B 5/741* (2013.01); *G06N 20/00* (2019.01)

(58) Field of Classification Search
CPC ..... G10L 21/0208; G10L 25/66; G10L 25/78; G10L 2025/783; G06N 20/00; A61B 5/0816; A61B 5/091; A61B 5/4803; A61B 5/7203; A61B 5/7264; A61B 5/7275; A61B 5/741
See application file for complete search history.

(56) References Cited

U.S. PATENT DOCUMENTS

| | | | |
|---|---|---|---|
| 2008/0119980 A1* | 5/2008 | Ross | G10L 15/01 701/31.4 |
| 2016/0005320 A1* | 1/2016 | deCharms | A61B 8/0808 434/236 |
| 2016/0283860 A1* | 9/2016 | Pycock | H04N 21/4788 |
| 2018/0018984 A1* | 1/2018 | Dickins | G10L 21/0232 |

(Continued)

*Primary Examiner* — Michelle M Koeth
*Assistant Examiner* — Paul J. Mueller
(74) *Attorney, Agent, or Firm* — Cognition IP, P.C.; Edward Steakley; Rajesh Fotedar

(57) ABSTRACT

Various embodiments of an apparatus, methods, systems and computer program products described herein are directed to a Voice Analysis Engine. According to various embodiments, the Voice Analysis Engine receives first streaming prompt data from a computing device. The Voice Analysis Engine analyzes the first streaming prompt data to provide feedback to the user of the computing device. Upon determining the first streaming prompt data satisfies one or more criteria, the Voice Analysis Engine receives second streaming prompt data from the computing device. The Voice Analysis Engine analyzes the streaming prompt data to predict a respiratory state of the user of the computing device.

16 Claims, 7 Drawing Sheets

(56) References Cited

U.S. PATENT DOCUMENTS

| | | | |
|---|---|---|---|
| 2018/0130473 A1* | 5/2018 | Odinak | G06F 21/32 |
| 2019/0088367 A1* | 3/2019 | Stamatopoulos | G16H 50/70 |
| 2021/0145306 A1* | 5/2021 | Karankevich | G16H 40/67 |

* cited by examiner

250

212
User Effort Index Frame-by-Frame Analysis

**206-1 – 206-*n***
Vocal Action Frames to Completion

252
Cross-sectional Analysis Mode

254
Longitudinal Analysis Mode

FIG. 2B

SYSTEMS AND METHODS FOR ANALYZING AND MONITORING LUNG FUNCTION USING VOICE AND BREATH SOUND SAMPLES FOR RESPIRATORY CARE

CROSS-REFERENCE TO RELATED APPLICATIONS

This application claims the benefit of U.S. Provisional Application No. 62/941,477, filed Nov. 27, 2019, which is hereby incorporated by reference in its entirety.

This application is a continuation-in-part of U.S. patent application Ser. No. 16/931,429, filed on Jul. 16, 2020, "METHODS AND SYSTEMS FOR VOICE PROFILING AS A SERVICE," which is hereby incorporated by reference in its entirety.

BACKGROUND

Lungs are the largest internal organ in the body and the only internal organ constantly exposed to the environment. The lungs' intake of oxygen and removal of carbon dioxide is called gas exchange. Gas exchange is part of breathing. Breathing is a vital function of life; breathing helps the human body work properly. Chronic lung diseases, such as asthma, chronic obstructive pulmonary disease (COPD), interstitial lung disease, pulmonary hypertension, cystic fibrosis, chronic pneumonia and lung cancer kill hundreds of millions of people every year and affect millions more. These diseases erode the health and well-being of the patients and have a negative impact on families and societies. These diseases are complex and heterogeneous. "Complex" means that they have several components with non-linear dynamic interactions, whereas "heterogeneous" indicates that not all of these components are present in all patients or, in a given patient, at all points. This dynamic complexity and heterogeneity explains and justifies the need for a precision medicine approach aimed at improving their assessment, treatment, and outcomes. Chronic lung diseases are not adequately diagnosed, treated or managed, with exacerbations often leading to hospitalization and even death, so that they are a major cause of morbidity and mortality. They are also costly, with COPD-related medical costs alone estimated at $32 billion in the United States in 2010 and an additional $4 billion in absenteeism costs.

SUMMARY

A current challenge in the diagnosis, treatment and management of chronic lung diseases is the inherent subjectivity and variability of detection, measurement and assessment. Various embodiments of an apparatus, methods, systems and computer program products described herein are directed to a Voice Analysis Engine. According to various embodiments, the Voice Analysis Engine analyzes and monitors lung function using voice and breath sound samples for personalized and precision respiratory care. The Voice Analysis Engine receives first streaming prompt data from a computing device. The Voice Analysis Engine analyzes the first streaming prompt data to provide feedback to the user of the computing device about the background noise, if it proves unacceptable.

Another major challenge in measuring and monitoring lung function is that it is dependent on user effort and technique. Unlike other medical vital statistics like body temperature, heart rate and blood pressure, lung function measurement and monitoring needs active user effort to be expended. The Voice Analysis Engine analyzes user voice and breath in real time to provide real time feedback to ensure best user effort. Upon determining the first streaming prompt data satisfies one or more criteria, the Voice Analysis Engine receives second streaming prompt data from the computing device. The Voice Analysis Engine analyzes the second streaming prompt data to predict a respiratory state of the user of the computing device. It is understood that the first and second streaming prompt data include frames of audio data representing one or more vocal actions performed by a speaker (i.e. the user of the computing device).

During a first phase, the Voice Analysis Engine performs real-time, frame-by-frame analysis of the incoming streaming audio data in order to determine whether to provide the user with feedback during their performance of certain types of vocal actions in response to prompts. For example, feedback may instruct the user to change a physical location due to background noise. Feedback may also instruct the user to increase their effort in performing one or more vocal actions. Such feedback may be determined and sent back to the user while the user is performing a respective vocal action in response to a prompt.

During the first phase, one or more embodiments of the Voice Analysis Engine performs real-time, frame-by-frame analysis of the incoming calibration audio data to detect presence of acceptable background noise level. The Voice Analysis Engine may further detect whether a user is following prompt instructions correctly and provide notifications to the user while the user is performing a vocal action(s). Various embodiments of the Voice Analysis Engine may further predict, determine and/or calculate one or more lung function metrics based on one or more vocal action audio data frames received during the first phase.

During a second phase, the Voice Analysis Engine receives additional incoming streaming audio data in order to predict various respiratory states of the user. The additional incoming streaming audio data includes additional audio data representative of performance of vocal and/or breathing actions in response to other prompts. The Voice Analysis Engine analyzes the additional incoming streaming audio data to provide the user with prediction output. According to various embodiments, the prediction output may represent one or more of metrics for lung function, estimated lung age, a breathlessness metric and/or detected changes in the user's voice that may trigger a notification that a current respiratory state or condition of the user is getting worse and/or exacerbated.

It is understood that privacy and security functionalities may be included in all embodiments described herein in order to anonymize personal identification data and health data of users in order to protect the privacy of users. For example, for an implementation of the Voice Analysis Engine via a cloud-based platform, data sent to and from Voice Analysis Engine modules may be anonymized and/or encrypted prior to receipt and transmission. In addition, any personal identification data and health data stored via the cloud-based platform may be further scrubbed of unique identifiers that a $3^{rd}$-party may use to identify an user(s).

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIG. 2B is a diagram illustrating an exemplary environment in which some embodiments may operate.

DETAILED DESCRIPTION

Figure 1A:
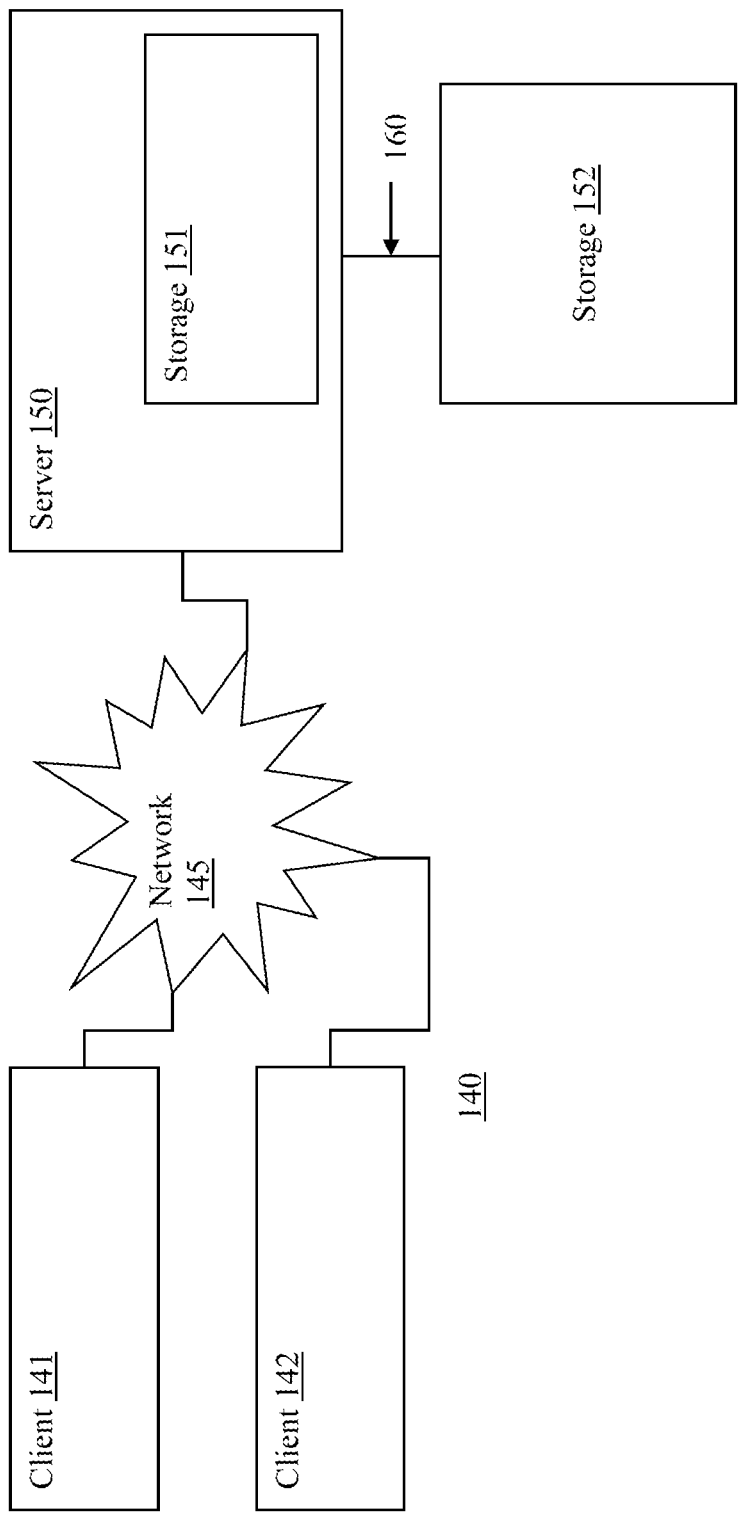
FIG. 1A is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
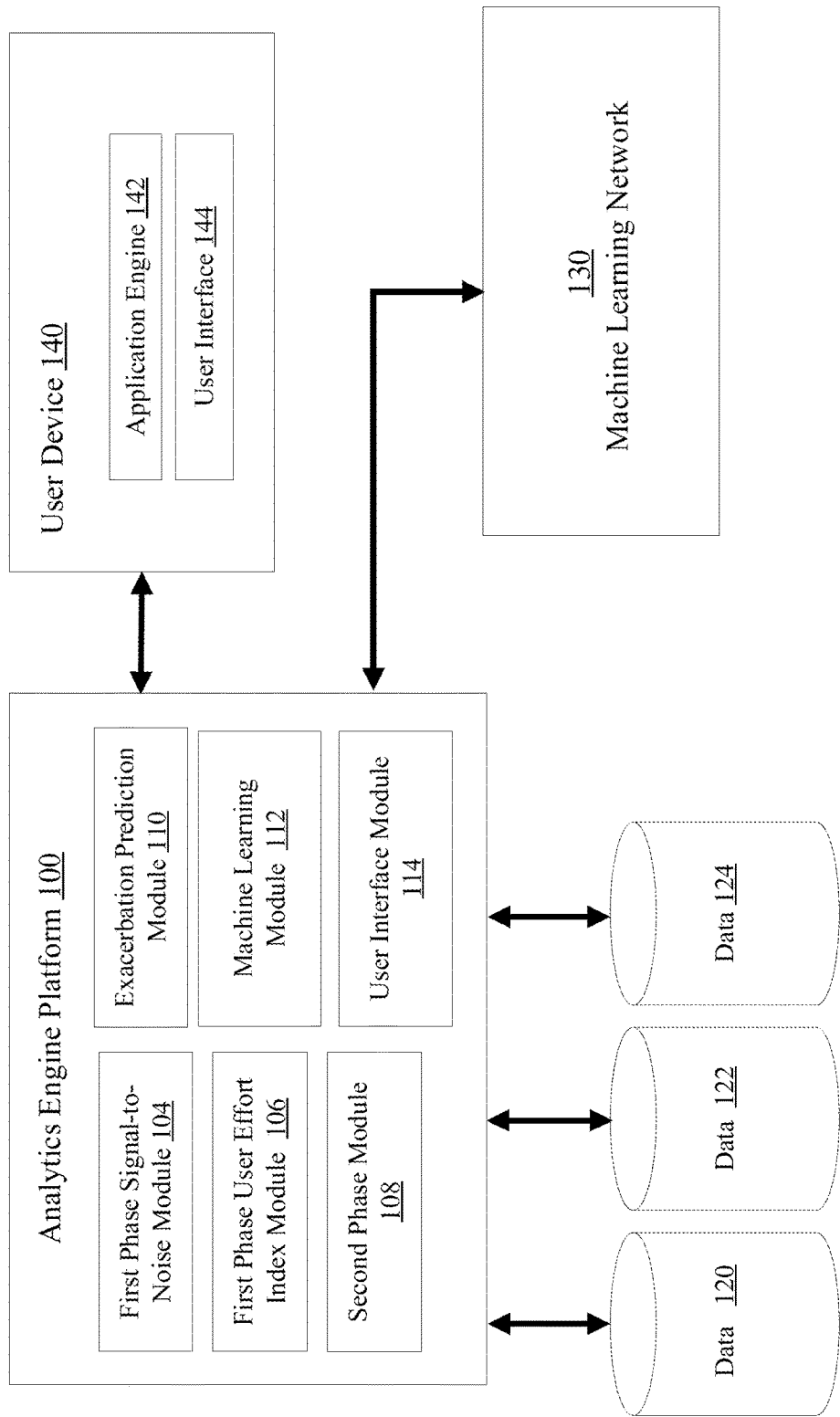
FIG. 1B is a diagram illustrating an exemplary environment in which some embodiments may operate.

FIG. 1B illustrates a block diagram of an example system 100 for Voice Analysis Engine that includes a Signal-to-Noise module 104, a User Effort Index module 106, a Second Phase module 108, an Exacerbation Prediction module 110, a Machine Learning module 112 and a user interface (U.I.) module 114. The system 100 may communicate with a user device 140 to display output, via a user interface 144 generated by an application engine 142.

Figure 2A:
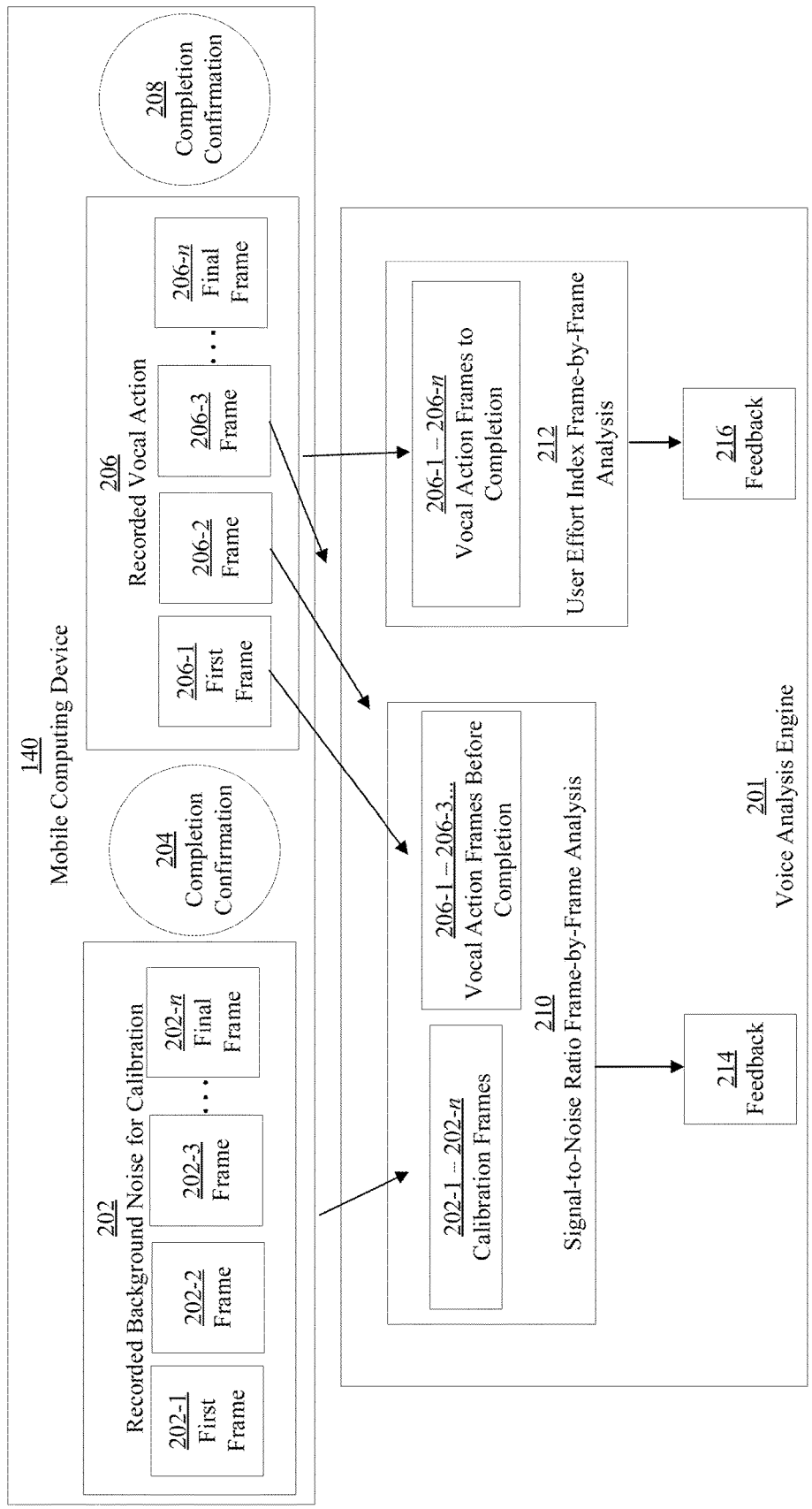
FIG. 2A is a diagram illustrating an exemplary environment in which some embodiments may operate.
Figure 3:
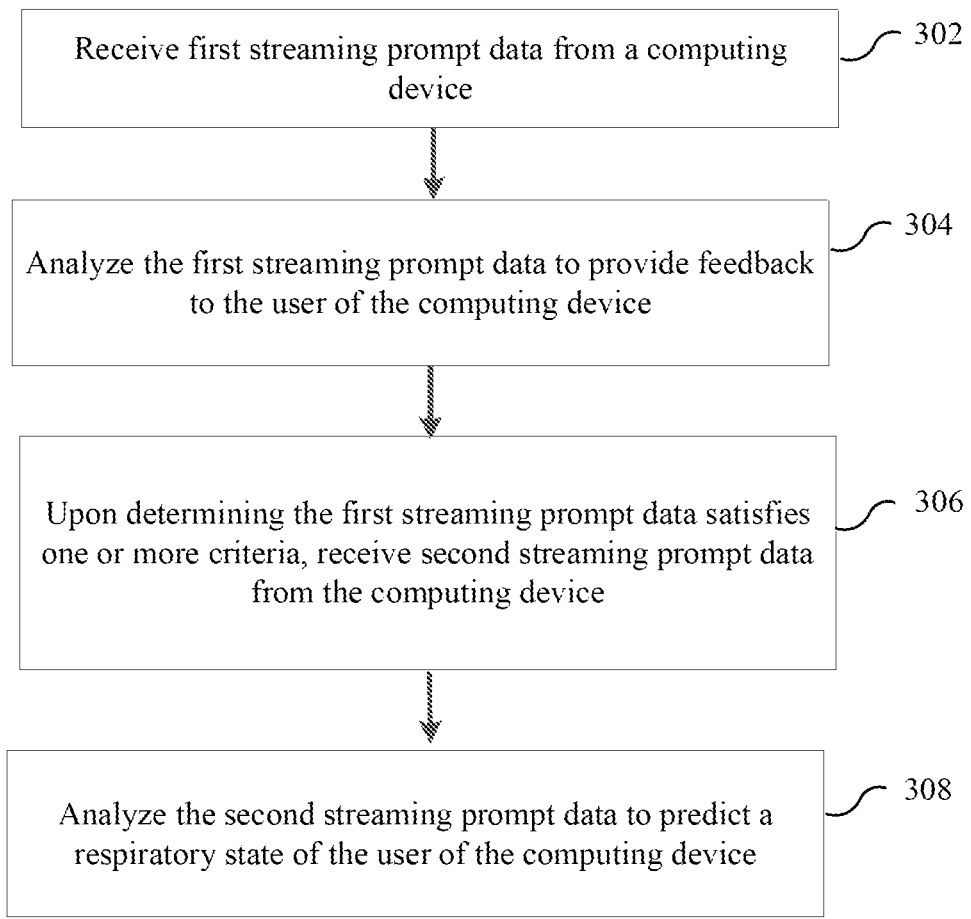
FIG. 3 is a diagram illustrating an exemplary method that may be performed in some embodiments.

The Signal-to-Noise module 104 of the system 100 may perform functionality as illustrated in FIGS. 2A, 2B and 3.

The User Effort Index module 106 of the system 100 may perform functionality illustrated in FIGS. 2A, 2B and 3.

Figure 4:
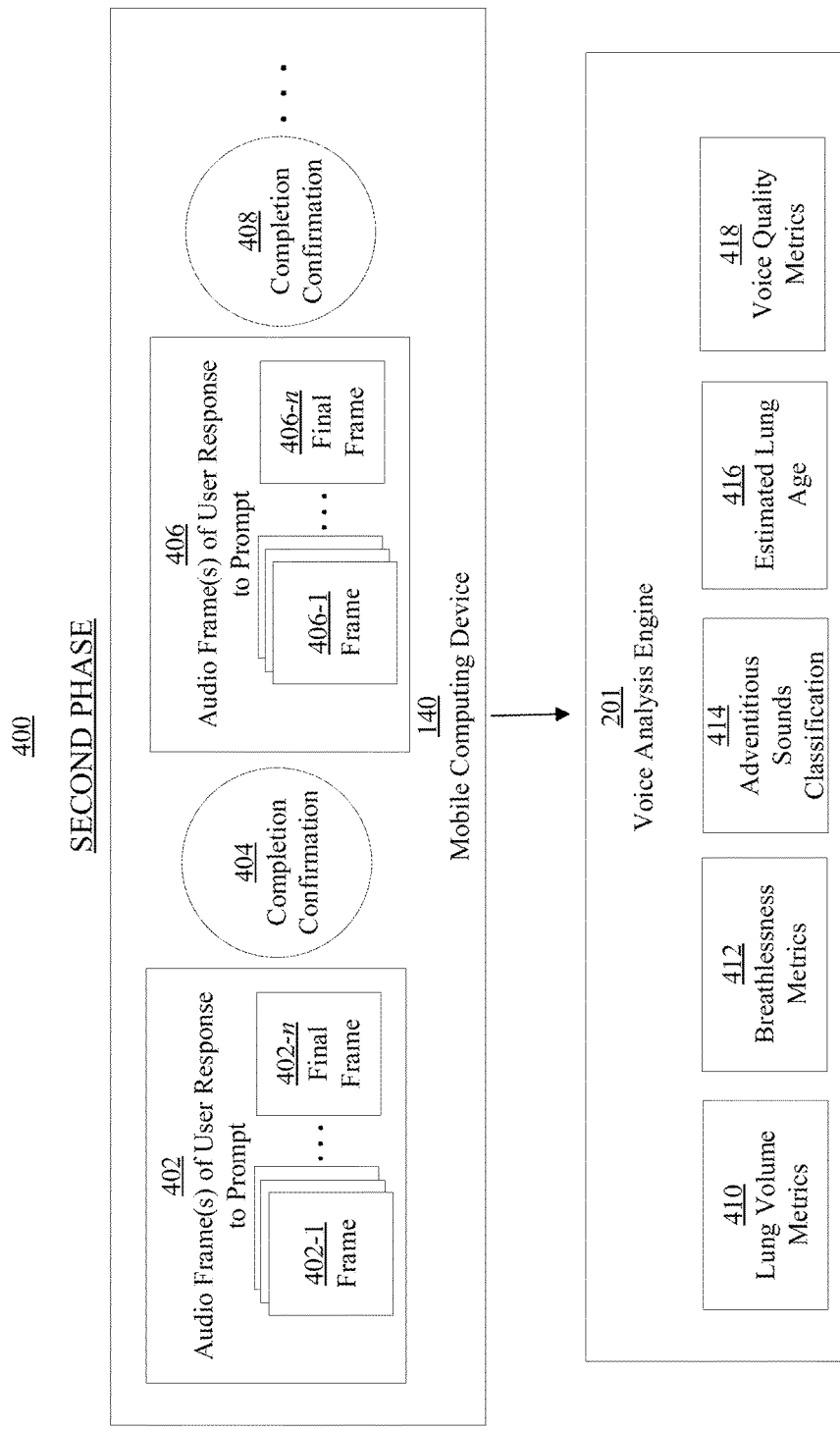
FIG. 4 is a diagram illustrating an exemplary environment in which some embodiments may operate.

The Second Phase module 108 of the system 100 may perform functionality illustrated in FIGS. 3 and 4.

The Exacerbation Prediction module 110 of the system 100 may perform functionality as illustrated in FIGS. 3 and 4.

The Machine Learning module 112 of the system 100 may perform functionality as illustrated in FIGS. 2A, 2B, 3 and 4. The Machine Learning module 112 may further train a machine learning network 130 that includes one or more machine learning models to generate output from functionality as illustrated in FIGS. 2A, 2B, 3 and 4.

The user interface (U.I.) module 114 of the system 100 may display information, display one or more relationships, predictions, graphs, and insights data generated based on functionality as illustrated in FIGS. 2A, 2B, 3 and 4.

While the databases 120, 122 and 124 are displayed separately, the databases and information maintained in a database may be combined together or further separated in a manner the promotes retrieval and storage efficiency and/or data security.

According to various embodiments, the Voice Analysis Engine may be deployed via a cloud computing platform accessible by one or more computing devices associated with a plurality of users. A computing device (such as a smartphone) of an end user may run one or more software modules compatible with the Voice Analysis Engine.

As shown in diagram 200 of FIG. 2A, according to various embodiments, the Voice Analysis Engine 201 analyzes frames of audio data 202-1, 202-2, 202-3 . . . 202-n, 206-1, 206-2, 206-3 . . . 206-n of first streaming prompt data in real-time on a frame-by-frame basis before the user completes a vocal response to a prompt for a vocal action to be performed at the computing device. A frame of audio data may be pre-defined as any audio data that occurs for a selected period of time, such as—for example—each frame may include 10 milliseconds of audio data.

First streaming prompt data corresponds to frames of calibration audio data 202-1, 202-2, 202-3 . . . 202-n of background noise occurring in response to a first calibration prompt for the user to remain silent. When the user has been silent for a given duration of time, the user provides input 204 to the computing device 140 that a response to the first calibration prompt is complete. First streaming prompt data further includes frames of audio data 206-1, 206-2, 206-3 . . . 206-n of a recorded vocal action occurring in response to a subsequent second prompt for the vocal action to be performed by user of the computing device. When the user has performed the vocal action for a given duration of time, the user provides input 208 to the computing device 140 that a response to the subsequent second prompt is complete.

The Voice Analysis Engine 201 performs signal-to-noise ratio analysis 210 on a frame-by-frame basis as it receives calibration audio frames of background noise 202-1 . . . 202-n and one or more audio frames 206-1 of the recorded vocal action. However, the Voice Analysis Engine 201 completes signal-to-noise ratio analysis 210 before the final audio frame 206-n of the recorded vocal action is received. In some embodiments, signal-to-noise ratio analysis 210 may be complete upon analysis of the first frame of the recorded vocal action 206-1. For example, during signal-to-noise ratio analysis 210, the Voice Analysis Engine 201 generates a spectrogram for each audio frame 202-1 . . . 202-n, 206-1 . . . 206-3 . . . as each respective frame is received and determines the signal power represented in each frame's spectrogram.

The Voice Analysis Engine 201 computes an average signal power of the background noise in the calibration audio frames 202-1 . . . 202-n. The Voice Analysis Engine 201 similarly computes the average signal power of the vocal action audio frames 206-1, 206-2, 206-3 . . . generated and transmitted by the computing device 140 as the user performs the vocal action. The Voice Analysis Engine 201 continually calculates the ratio of the average signal power of the calibration audio frames 202-1 . . . 202-n to the average signal power of the incoming recorded vocal action audio frames 206-1, 206-2, 206-3 . . . and sends one or more instances of feedback 214 to the user's computing device 140 if the signal-to-noise ratio dips below 6 decibels. For example, the feedback 214 may be an instruction to move to a quieter physical location. Once the user has moved to a quieter physical location, the change in the average signal power of subsequent incoming recorded vocal action audio frames 206-3 . . . may result in a higher signal-to-noise ratio with respect to the average signal power of the calibration audio frames 202-1 . . . 202-n.

The signal-to-noise ratio analysis 210 will continually calculate the signal-to-noise ratio as additional vocal action audio frames 206-3 . . . are received and will continually provide respective instance(s) of feedback 214 to notify the user to change a current physical location whenever the signal-to-noise ratio is below 6 decibels or above 15 decibels. If the signal-to-noise ratio stays above 15 decibels for a certain pre-defined amount of time, the Voice Analysis Engine 201 sends additional feedback 214 indicating the user is currently at an acceptable physical location.

The Voice Analysis Engine 201 performs user effort index analysis 212 on a frame-by-frame basis as it receives audio frames of the recorded vocal action 206-1 . . . 206-n. However, user effort index analysis 212 is complete upon analysis of the final frame of the recorded vocal action 206-n. As respective audio frames of the recorded vocal action 206-1 . . . 206-n are received by the Voice Analysis Engine 201, user effort index analysis 212 generates one or more instances of feedback 216 sent back to the user's computing device 140. Such feedback 216 may provide a notification to the user to perform the vocal action with more or less effort. Such feedback 216 may provide a notification to the user that the user's effort in performing the vocal action is currently acceptable.

As shown in diagram 250 of FIG. 2B, the user effort index analysis 212 includes two modes: a cross-sectional analysis mode 252 and a longitudinal analysis mode 254. Both modes 252, 254 require all the respective audio frames of the recorded vocal action 206-1 . . . 206-n. During the cross-sectional analysis mode 252, the Voice Analysis Engine 201 determines a duration of time in which the user was able to perform the vocal action. For example, how long the user was able to sustain the syllable of "Aaaah." The cross-sectional analysis mode 252, determines a phonation demographic ratio (PDR) based on how long the user sustained the vocal action as compared to the lower limit duration of those people in the same demographic as the user. If the (PDR) is below a threshold value, such as for example 0.5, the Voice Analysis Engine 201 sends feedback to the computing device 140 to provide a notification to the user to perform the vocal action again with more effort.

During the longitudinal analysis mode 254, the Voice Analysis Engine 201 receives input selected by the user that represents a set of current symptoms of the user. The longitudinal analysis mode 254 calculates a current symptom score based on the selected input and calculates a weight for the current symptom score. The Voice Analysis Engine 201 accesses one or more files that include previous symptom score weights from previous sessions of the user and vocal action durations that correspond to a recorded vocal action performed by the user during those previous sessions. The longitudinal analysis mode 254 calculates a mean (or average) value for the user based on the vocal action durations and symptom score weights of previous sessions of the user. The longitudinal analysis mode 254 calculates a user effort index based on a ratio according to [current symptom score weight*duration of current vocal action]/Mean (previous session weights*previous session vocal action duration). The Voice Analysis Engine 201 determines whether the user effort index of the user is acceptable based on comparing the user effort index to one or more thresholds.

According to some embodiments, the Voice Analysis Engine 201 detects an unacceptable background noise level on a frame-by-frame basis based on analysis of a subset of the calibration audio frames 202-1-202n. For example, the presence of an unacceptable background noise level can be determined without any of the recorded vocal action frames 206-1-206-n. In some embodiments, the Voice Analysis Engine 201 detects if the user is following instructions for prompt(s), if the Signal-to-Noise ratio is acceptable and also measure the user's effort index in real-time. The Voice Analysis Engine 201 may also calculate one or more lung function metrics (i.e. metrics 410, 412, 414) based on at least a portion of the recorded vocal action frames 206-1-206-n.

According to some embodiments, the Voice Analysis Engine 201, may detect whether the user is following one or more prompt instructions correctly. For example, during performance of the vocal action that corresponds to recorded vocal action frames 206-1 . . . , the Voice Analysis Engine 201 may be trained to detect audio that represents sound indicative of an inhalation at the outset of performing the vocal action. If presence of inhalation audio is not present in the early frames of the recorded vocal action frames 206-1 . . . (i.e. within a certain define amount of time at the beginning of the vocal action), Voice Analysis Engine 201 may send additional feedback as a notification to the user to instruct the user to start over.

As shown in flowchart 300 of FIG. 3, the Voice Analysis Engine receives first streaming prompt data from a computing device (Act 302). According to various embodiments, a user may be instructed to perform various vocal actions in response to respective sequential prompts. Each vocal action performed by the user may be recorded and represented in audio data streamed to the Voice Analysis Engine. Various embodiments of the Voice Analysis Engine may be implemented on a cloud computing platform. The audio data is received by the Voice Analysis Engine as an incoming stream that represents vocal actions performed by the user. A first phase involves receipt of the first streaming prompt data that includes audio data representing user responses to a calibration prompt to remain silent and a subsequent prompt to perform a pre-defined vocal action. The Voice Analysis Engine analyzes the first streaming prompt data to provide feedback to the user of the computing device (Act 304).

During the first phase, the Voice Analysis Engine generates the feedback with respect to whether the user has completed a vocal action at the computing device in response to a vocal action prompt and sends the feedback to the computing device. The Voice Analysis Engine generates the feedback based on analyzing one or more frames of audio data representing a portion(s) of the vocal action. For example, the Voice Analysis Engine may generate feedback while the user is performing a vocal action based on analysis of one or more frames of audio data representing a portion of the performance of that same vocal action.

Generating the feedback may include calculating a signal-to-noise ratio before the user completes a particular vocal action. The Voice Analysis Engine also calculates a user effort index for the user upon completion of the same particular vocal action. The Voice Analysis Engine calculates a signal-to-noise ratio of the first streaming prompt data based on analyzing the audio data responsive to a first calibration prompt (i.e. to remain silent) and audio frame(s) in the audio data responsive to a subsequent second prompt (i.e. say "aaaah") for a vocal action. The feedback is generated before the user completes the vocal action in response to the subsequent second prompt at the computing device. For example, the Voice Analysis Engine provides the user with a notification to move to a physical location with less background noise after the user has begun performing the "aaaah" vocal action—but before the user completes the "aaaah" vocal action.

According to various embodiments, feedback may be based on a measure of the user's vocal and/or respiratory effort. For example, the Voice Analysis Engine provides the user with a notification to "try harder" and/or "put more effort" in response to a prompt for a vocal action. According to various embodiments, the feedback based on the user's vocal and/or respiratory effort may be based analysis of one or more frames representing the user performing the "aaaah" vocal action, which is finalized when the user's completes the "aaaah" vocal action. It is understood that various embodiments are not limited to the vocal action of performance of the long syllable "aaaah." Various embodiments may include any type of prompt for the user to perform any type of vocal action(s) and/or respiratory action(s).

Upon determining the first streaming prompt data satisfies one or more criteria (i.e. there is an acceptable level of background noise and user effort), the Voice Analysis Engine receives subsequent second streaming prompt data from the computing device (Act 306). The Voice Analysis Engine analyzes this second streaming prompt data to predict (i.e. infer, determine, detect) a respiratory state of the user of the computing device (Act 308).

It is understood that some of the acts of the exemplary flowchart 300 may be performed in different orders or in parallel. Also, one or more of the acts in the exemplary flowchart 300 may occur in two or more computers, for example if the method is performed in a networked environment. Various acts may be optional. Some acts may occur on local computer with other acts occur on a remote computer.

As shown in FIG. 4, during the second phase, the Voice Analysis Engine 201 analyzes the streaming prompt data 404, 406 to determine an user's estimate lung age 410, various lung volume metrics 412 (FEV1, FVC, FEV1/FVC, Obstruction), one or more metrics of breathlessness 414, adventitious sounds classification 416 and to predict whether a condition or disease of the user is being exacerbated based on voice quality metrics 418. The streaming prompt data may include respective audio frames 402-1 . . . 402-n, 406-1 . . . 406-n and input data 404, 408 selected by the user confirmation confirming that a respective response to a prompt(s) is complete. The various types of prompts and vocal actions in response to the prompts may include prompts and responses described in U.S. patent application Ser. No. 16/931,429, filed on Jul. 16, 2020, "METHODS AND SYSTEMS FOR VOICE PROFILING AS A SERVICE," which is hereby incorporated by reference in its entirety.

To determine the lung volume metrics 410, the breathlessness metrics 412 (i.e. segmenting out speech vs. non-speech, average number of pauses, average duration of pauses, word rate, phoneme rate, syllable rate) and adventitious sounds classification 414 (e.g. respiratory events such as coughing, wheezing, stridor, throat clearing, voice crackling), the Voice Analysis Engine 201 implements the first and second level segmentation as described in U.S. patent application Ser. No. 16/931,429, filed on Jul. 16, 2020, "METHODS AND SYSTEMS FOR VOICE PROFILING AS A SERVICE." The first and second level segmentation is performed in real-time on a frame-by-frame basis as one or more audio frames 402-1 . . . 402-n, 406-1 . . . 406-n are received by the Voice Analysis Engine 201. That is, the Voice Analysis Engine 201 initiates the first and second level segmentation as the audio frames are received 402-1 . . . 402-n, 406-1 . . . 406-n while the computing device 140 may be concurrently generating additional audio frames that correspond to a vocal action (or prompt response) currently being performed by the user.

The Voice Analysis Engine 201 employs one or more Linear and/or Non-Linear Regression models to determine the lung volume metrics 410, the breathlessness metrics 412 and the adventitious sounds classification 414. Various types of machine learning models utilized by the Voice Analysis Engine 201 may include one or more of: a Ridge Regressor and a Classifier(s) (Logistic, Support Vector Machines, Random Forest).

To determine the estimated lung age 416 of the user, the Voice Analysis Engine 201 utilizes the FVC (forced vital capacity) of the user from the lung volume metrics 410 and performs a binary search over lung data provided by the Global Lung Function Initiative (GLI) to identify an age or age range of individuals with a FVC closest to the FVC of the user. The Voice Analysis Engine 201 returns the identified age or age range as the user's estimated lung age 416.

The Voice Analysis Engine 201 determines whether a user's condition or known disease is exacerbated (or about to become exacerbated) by determine voice quality metrics 418. During various sessions, the user selects input representing answers for a COPD Assessment Test (CAT) and a CAT Score is determined based on the user's selected input. The Voice Analysis Engine 201 utilizes the user's audio frame data and corresponding CAT score from previous sessions in a comparison to the user's audio frame data and CAT score of a current session to determine whether the user may begin to experience exacerbation or deterioration of various symptoms. For example, audio frame data from a previous session may be a baseline voice sample recorded when the user's symptoms are considered stable. Audio frame data may also include a close-to-exacerbation voice sample recorded when the user had begun to be concerned about a possible worsening of symptoms. Other audio data may be based on various voice samples recorded by the user—such as daily voice samples associated with a corresponding CAT score. The Voice Analysis Engine 201 also includes as input a duration of time between the current session and one or more previous sessions.

The Voice Analysis Engine 201 trains a machine learning model based on one or more features of voice samples and corresponding CAT scores associated with a plurality of users. The Voice Analysis Engine 201 detects differences in a user's current voice sample and voice sample training data to detect when the user will begin to experience a deterioration of one or more symptoms.

Figure 5:
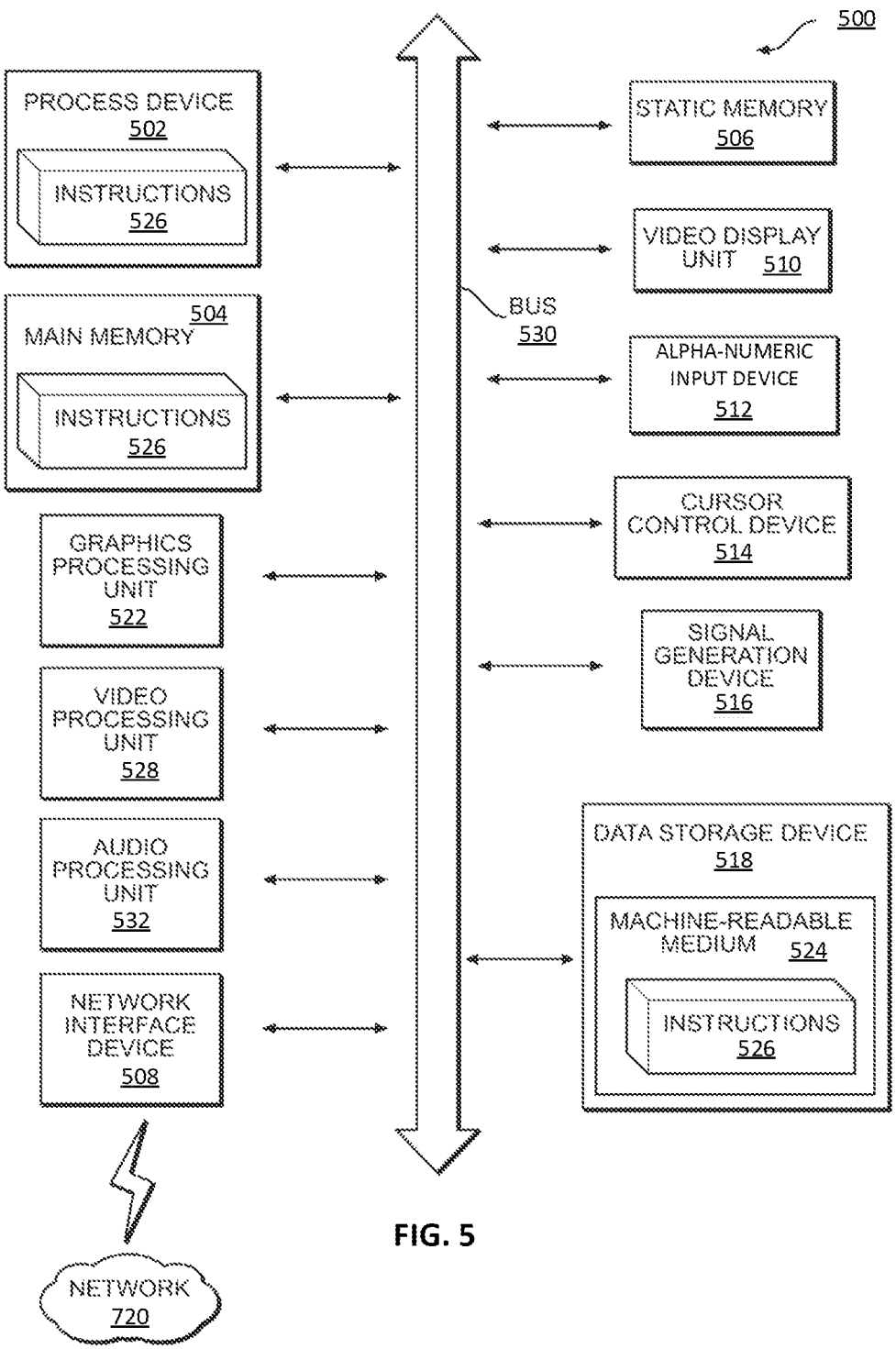
FIG. 5 is a diagram illustrating an exemplary environment in which some embodiments may operate.

FIG. 5 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 500 includes a processing device 502, a main memory 504 (e.g., read-only memory (ROM), flash memory, dynamic random access memory (DRAM) such as synchronous DRAM (SDRAM) or Rambus DRAM (RDRAM), etc.), a static memory 506 (e.g., flash memory, static random access memory (SRAM), etc.), and a data storage device 518, which communicate with each other via a bus 530.

Processing device 502 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. The processing device 502 is configured to execute instructions 526 for performing the operations and steps discussed herein.

The computer system 500 may further include a network interface device 508 to communicate over the network 520. The computer system 500 also may include a video display unit 510 (e.g., a liquid crystal display (LCD) or a cathode ray tube (CRT)), an alphanumeric input device 512 (e.g., a keyboard), a cursor control device 514 (e.g., a mouse), a graphics processing unit 522, a signal generation device 516 (e.g., a speaker), graphics processing unit 522, video processing unit 528, and audio processing unit 532.

The data storage device 518 may include a machine-readable storage medium 524 (also known as a computer-readable medium) on which is stored one or more sets of instructions or software 526 embodying any one or more of the methodologies or functions described herein. The instructions 526 may also reside, completely or at least partially, within the main memory 504 and/or within the processing device 502 during execution thereof by the computer system 500, the main memory 504 and the processing device 502 also constituting machine-readable storage media.

In one implementation, the instructions 526 include instructions to implement functionality corresponding to the components of a device to perform the disclosure herein. While the machine-readable storage medium 524 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general-purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:
receiving first streaming prompt data from a computing device;
analyzing the first streaming prompt data in real-time on a frame-by-frame basis;
providing feedback to a user of the computing device based on analysis of the first streaming prompt data;
upon determining the first streaming prompt data satisfies one or more criteria, receiving at least a subset of second streaming prompt data from the computing device, the subset of the second streaming prompt data comprising audio data representative of a first performed portion of a vocal action by the user; and
analyzing, prior to completion by the user of performance of one or more subsequent portions of the same vocal action, the subset of the second streaming prompt data for generation of a prediction of a respiratory state of the user of the computing device, wherein analyzing the subset of the second streaming prompt data further comprises:
analyzing audio data of the subset of the second streaming prompt data in real-time on the frame-by-frame basis;
wherein providing feedback comprises:
generating feedback at the computing device for the user, based on analysis of the subset of the second streaming prompt data.

2. The computer-implemented method of claim 1, wherein analyzing the first streaming prompt data to provide feedback to the user of the computing device comprises:
generating the feedback with respect to whether the user has completed a respective vocal action at the computing device in response to a vocal action prompt associated with the first streaming prompt data; and
sending the feedback to the computing device.

3. The computer-implemented method of claim 1 further comprising:
detecting an unacceptable background noise level based on analysis of the first streaming prompt data;
calculating a signal-to-noise ratio before the user completes the vocal action based on analysis of at least the subset of the second streaming prompt data;
calculating a user effort index for the user upon completion of the vocal action; and
detecting that the user has correctly performed the instructions for the vocal action.

4. The computer-implemented method of claim 1, wherein the first streaming prompt data corresponds to audio data occurring in response to a first calibration prompt for the user of the computing device to remain silent; and
wherein the second streaming prompt data comprises:
audio data occurring in response to a subsequent prompt for the vocal action to be performed by the user of the computing device; and
wherein analyzing the first streaming prompt data to provide feedback to the user of the computing device further comprises:

detecting a presence of unacceptable background noise level based on analysis of one or more calibration audio data frames prior to receipt of a respective recorded vocal action audio data frame corresponding to the first streaming prompt data.

5. The computer-implemented method of claim 4, wherein analyzing audio data of the first streaming prompt data in real-time on a frame-by-frame basis comprises:
calculating a signal-to-noise ratio of a voice signal in the second streaming prompt data to a noise profile from the first streaming prompt data based on analyzing the audio data responsive to the first calibration prompt and;
wherein the second streaming prompt data comprises:
at least one audio frame in the audio data responsive to the subsequent prompt for the vocal action.

6. The computer-implemented method of claim 1, wherein analyzing the subset of the second streaming prompt data to predict a respiratory state of the user of the computing device comprises:
training a machine learning model comprising:
receiving a baseline voice sample of the user acquired at a first time when one or more symptoms of the user were stable and receiving a first symptoms assessment score associated with the baseline voice sample;
receiving a close-to-exacerbation (exacerbated) voice sample of the user acquired at a second time when the symptoms may have begun to become exacerbated and receiving a second symptoms assessment score associated with the exacerbated voice sample;
receiving a plurality of additional voice samples of the user acquired at respective different times and receiving a symptoms assessment score that corresponds with a given additional voice sample; and
including as training data, at least in part, the user's demographics, baseline voice sample, exacerbated voice sample, additional voice samples and respective corresponding symptoms assessment score.

7. The computer-implemented method of claim 6, further comprising:
receiving a current voice sample of the user;
feeding as input into the machine learning model the current voice sample to predict when the user may begin to experience an exacerbation.

8. A system comprising:
one or more processors; and
a non-transitory computer readable medium storing a plurality of instructions, which when executed, cause the one or more processors to:
receive first streaming prompt data from a computing device;
analyze the first streaming prompt data in real-time on a frame-by-frame basis;
provide feedback to a user of the computing device based on analysis of the first streaming prompt data;
upon determining the first streaming prompt data satisfies one or more criteria, receive at least a subset of second streaming prompt data from the computing device, the subset of the second streaming prompt data comprising audio data representative of a first performed portion of a vocal action by the user; and
analyze, prior to completion by the user of performance of one or more subsequent portions of the same vocal action, the subset of the second streaming prompt data for generation of a prediction of a respiratory state of the user of the computing device, wherein analyze the subset of the second streaming prompt data further comprises:
analyze audio data of the subset of the second streaming prompt data in real-time on the frame-by-frame basis;
wherein provide feedback comprises:
generate feedback at the computing device for the user, based on analysis of the subset of the second streaming prompt data.

9. The system of claim 8, wherein analyze the first streaming prompt data to provide feedback to the user of the computing device comprises:
generate the feedback with respect to whether the user has completed a respective vocal action at the computing device in response to a vocal action prompt associated with the first streaming prompt data; and
sending the feedback to the computing device.

10. The system of claim 9, further comprising:
detect an unacceptable background noise level based analysis of the first streaming prompt data;
calculate a signal-to-noise ratio before the user completes the vocal action based on analysis of at least the subset of the second streaming prompt data;
calculate a user effort index for the user upon completion of the vocal action; and
detect that the user has correctly performed the instructions for the vocal action.

11. The system of claim 10, wherein the first streaming prompt data corresponds to audio data occurring in response to a first calibration prompt for the user of the computing device to remain silent and;
wherein the second streaming prompt data comprises:
audio data occurring in response to a subsequent prompt for the vocal action to be performed by the user of the computing device.

12. The system of claim 11, wherein analyze audio data of the second streaming prompt data in real-time on a frame-by-frame basis comprises:
calculate a signal-to-noise ratio of a voice signal in one or more frames of the second streaming prompt data and a noise profile from the first streaming prompt data based on analyzing the audio data responsive to the first calibration prompt and;
wherein the subset of the second streaming prompt data comprises:
at least one audio frame in the audio data responsive to the subsequent prompt for the vocal action.

13. The system of claim 8, wherein analyze the subset of the second streaming prompt data to predict a respiratory state of the user of the computing device comprises:
train a machine learning model comprising:
receive a baseline voice sample of the user acquired at a first time when one or more symptoms of the user were stable and receiving a first symptoms assessment score associated with the baseline voice sample;
receive a close-to-exacerbation (exacerbated) voice sample of the user acquired at a second time when the symptoms may have begun to become exacerbated and receiving a second symptoms assessment score associated with the exacerbated voice sample;
receive a plurality of additional voice samples of the user acquired at respective different times and receiving a symptoms assessment score that corresponds with a given additional voice sample; and
include as training data, at least in part, the user's demographics, baseline voice sample, exacerbated voice sample, additional voice samples and respective corresponding symptoms assessment score.

14. The system of claim 13, further comprising:
receive a current voice sample of the user;
feed as input into the machine learning model the current voice sample to predict when the user may begin to experience an exacerbation.

15. A computer program product comprising a non-transitory computer-readable medium having a computer-readable program code embodied therein to be executed by one or more processors, the program code including instructions to:
receive first streaming prompt data from a computing device, the first streaming prompt data comprising audio data representative of a user at the computing device refraining from currently performing any vocal action;
analyze a first portion of the first streaming prompt data, wherein analyze the first portion of the first streaming prompt data further comprises:
analyze audio data of the first portion of the first streaming prompt data in real-time on a frame-by-frame basis before the user initiates a vocal response to a prompt requesting performance of any type of vocal action;
provide feedback to the user of the computing device based on background noise level based on analysis of the first portion of the first streaming prompt data;
receive at least a subset of second streaming prompt data from the computing device, the subset of the second streaming prompt data comprising audio data representative of a first performed portion of the vocal response by the user; and
analyze, prior to completion by the user of performance of one or more subsequent portions of the same vocal response, the subset of the second streaming prompt data for generation of a prediction of a respiratory state of the user of the computing device, wherein analyze the subset of the second streaming prompt data further comprises:
analyze audio data of the subset of the second streaming prompt data in real-time on the frame-by-frame basis;
wherein providing feedback comprises:
generate feedback at the computing device for the user, based on analysis of the subset of the second streaming prompt data.

16. The computer program product of claim 15, wherein analyze the first streaming prompt data to provide feedback to the user of the computing device comprises:
detect an unacceptable background noise level based on analysis of the first portion of the first streaming prompt data;
upon determining the first streaming prompt data satisfies one or more criteria, receive second streaming prompt data from the computing device;
wherein analyze the subset of the second streaming prompt comprises:
generate the feedback with respect to whether the user has completed the vocal action at the computing device in response to a subsequent vocal action prompt; and
send the feedback to the computing device;
and
analyze the subset of the second streaming prompt data to predict a respiratory state of the user of the computing device, which further comprises:
train a machine learning model comprising:
(i) receive a baseline voice sample of the user acquired at a first time when one or more symptoms of the user were stable and receiving a first symptoms assessment score associated with the baseline voice sample;
(ii) receive a close-to-exacerbation (exacerbated) voice sample of the user acquired at a second time when the symptoms may have begun to become exacerbated and receiving a second symptoms assessment score associated with the exacerbated voice sample;
(iii) receive a plurality of additional voice samples of the user acquired at respective different times and receiving a symptoms assessment score that corresponds with a given additional voice sample; and
(iv) include as training data, at least in part, the user's demographics, baseline voice sample, exacerbated voice sample, additional voice samples and respective corresponding symptoms assessment score; and
wherein analyze the subset of the second streaming prompt data to predict a respiratory state of the user of the computing device further comprises:
(a) receive a current voice sample of the user;
(b) feed as input into the machine learning model the current voice sample to predict when the user may begin to experience an exacerbation.

* * * * *